(12) United States Patent
Kramer

(10) Patent No.: US 11,443,853 B2
(45) Date of Patent: *Sep. 13, 2022

(54) DYNAMIC ROLLING SEVETY OF ILLNESS SCORE FOR A CRITICALLY ILL PATIENT

(71) Applicant: Prescient Healthcare Consulting, LLC, Charlottesville, VA (US)

(72) Inventor: Andrew Alan Kramer, Charlottesville, VA (US)

(73) Assignee: Prescient Healthcare Consulting, LLC, Charlottesville, VA (US)

( * ) Notice: Subject to any disclaimer, the term of this patent is extended or adjusted under 35 U.S.C. 154(b) by 244 days.

This patent is subject to a terminal disclaimer.

(21) Appl. No.: 16/595,540

(22) Filed: Oct. 8, 2019

(65) Prior Publication Data
US 2020/0194124 A1 Jun. 18, 2020

Related U.S. Application Data

(60) Provisional application No. 62/779,694, filed on Dec. 14, 2018.

(51) Int. Cl.
*G16H 50/30* (2018.01)
*G16H 50/70* (2018.01)
(Continued)

(52) U.S. Cl.
CPC ........... *G16H 50/30* (2018.01); *A61B 5/0002* (2013.01); *G16H 50/70* (2018.01); *G16H 20/00* (2018.01)

(58) Field of Classification Search
CPC ... A61B 5/0022; A61B 5/7275; A61B 5/0002; G16H 50/30; G16H 50/70; G16H 20/00; G16H 70/20
See application file for complete search history.

(56) References Cited

U.S. PATENT DOCUMENTS 9,679,341 B2   6/2017   Kocis et al.
10,799,184 B2  10/2020  Kramer
(Continued)

FOREIGN PATENT DOCUMENTS

WO    2011115576 A2    9/2011

OTHER PUBLICATIONS

"Vocera communication badge", Retrieved from internet; https://we.archive.org/web/20160420232543/http:/www.vocera.com/product/vocera-communication-badge (Year: 2016); 11 pages.

(Continued)

*Primary Examiner* — Rex R Holmes
*Assistant Examiner* — Sana Sahand
(74) *Attorney, Agent, or Firm* — John H. Thomas, P.C.

(57) ABSTRACT

A system and method for creating and presenting a rolling severity of illness acuity score are comprised of two phases. The first phase analyzes historical physiologic and clinical data from a hospital's EMR system and discovers data patterns that presage a deleterious outcome. These data patterns are stored in a first database. Once these patterns have been revealed, the second phase involves embedding these patterns into a hospital's EMR, collecting data on new patients in near-real time, matching up this data against the patterns uncovered in Phase One, and producing a score based on how many of these deleterious patterns a patient is exhibiting. This score is updated continuously, weighting the current value higher than previous scores. If this rolling score surpasses a specific value, an alert is generated. The alert, in one example a color-coded signal, is then sent to a mobile device or tablet of the clinicians caring for the patient.

14 Claims, 3 Drawing Sheets

Schematic overview of the system and method

(51) Int. Cl.
*A61B 5/00* (2006.01)
*G16H 20/00* (2018.01)

(56) References Cited

U.S. PATENT DOCUMENTS

| | | | | |
|---|---|---|---|---|
| 2003/0060690 | A1* | 3/2003 | Jelliffe | G16H 50/70 600/300 |
| 2006/0149597 | A1* | 7/2006 | Powell | G16Z 99/00 705/2 |
| 2007/0112275 | A1* | 5/2007 | Cooke | A61B 5/352 600/513 |
| 2008/0004904 | A1* | 1/2008 | Tran | A61B 8/565 705/2 |
| 2011/0009714 | A1* | 1/2011 | Zong | A61B 5/021 600/301 |
| 2013/0116578 | A1* | 5/2013 | An | A61B 5/0205 600/484 |
| 2013/0197924 | A1* | 8/2013 | Kocis | G16Z 99/00 705/2 |
| 2014/0229200 | A1* | 8/2014 | Chan | A61B 5/08 705/3 |
| 2014/0350369 | A1 | 11/2014 | Budiman et al. | |
| 2016/0220127 | A1* | 8/2016 | Boyer | G16H 50/30 |
| 2016/0302674 | A1* | 10/2016 | Moyer | A61B 5/6833 |
| 2017/0249445 | A1 | 8/2017 | Devries et al. | |
| 2017/0262597 | A1* | 9/2017 | Huddar | G16H 50/20 |

OTHER PUBLICATIONS

YouTube video clip entitled "Vocera Patient Monitoring integration" Retrieved from Internet: https://www.youtube.com/watch?v=ZHnw8Xy3rm0 (Year:2012); 1 page.

\* cited by examiner

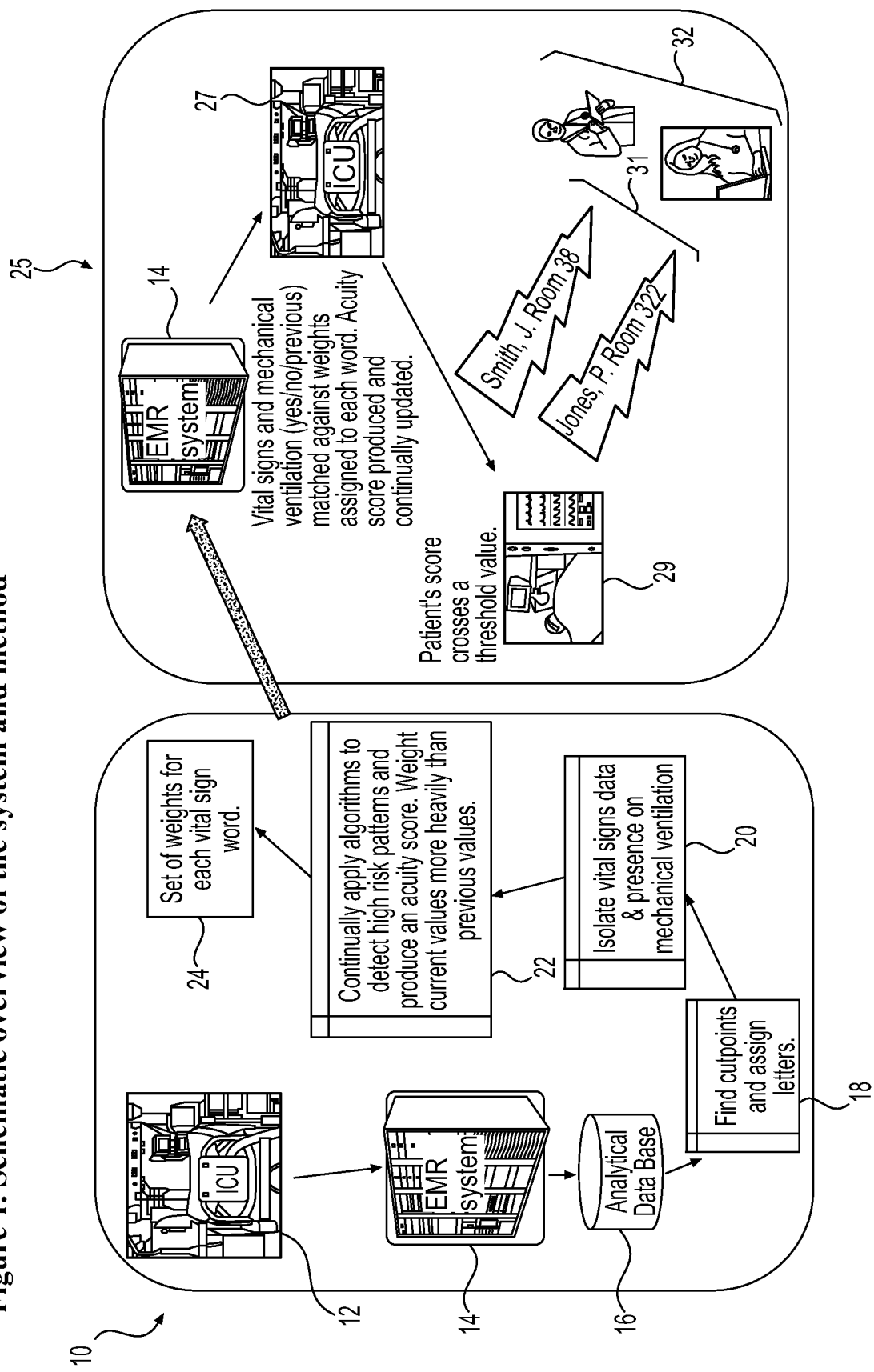
Figure 1. Schematic overview of the system and method

Figure 2. Mortality rate by five percent quantiles of maximum score. Development data set.
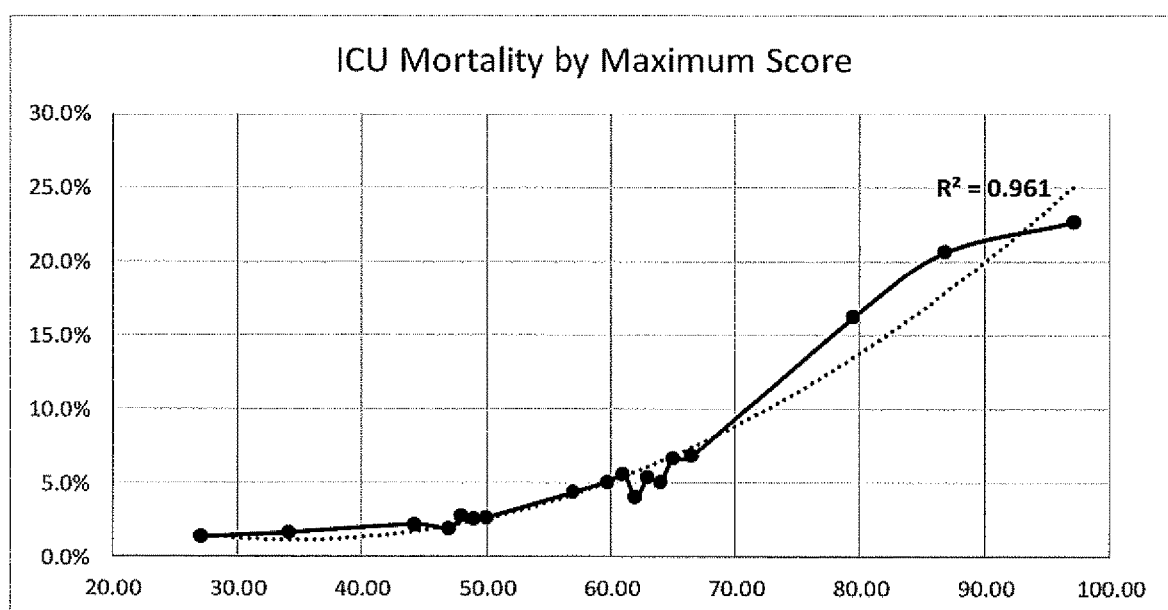

Figure 3. Mortality rate by five percent quantiles of maximum score. Validation data set.
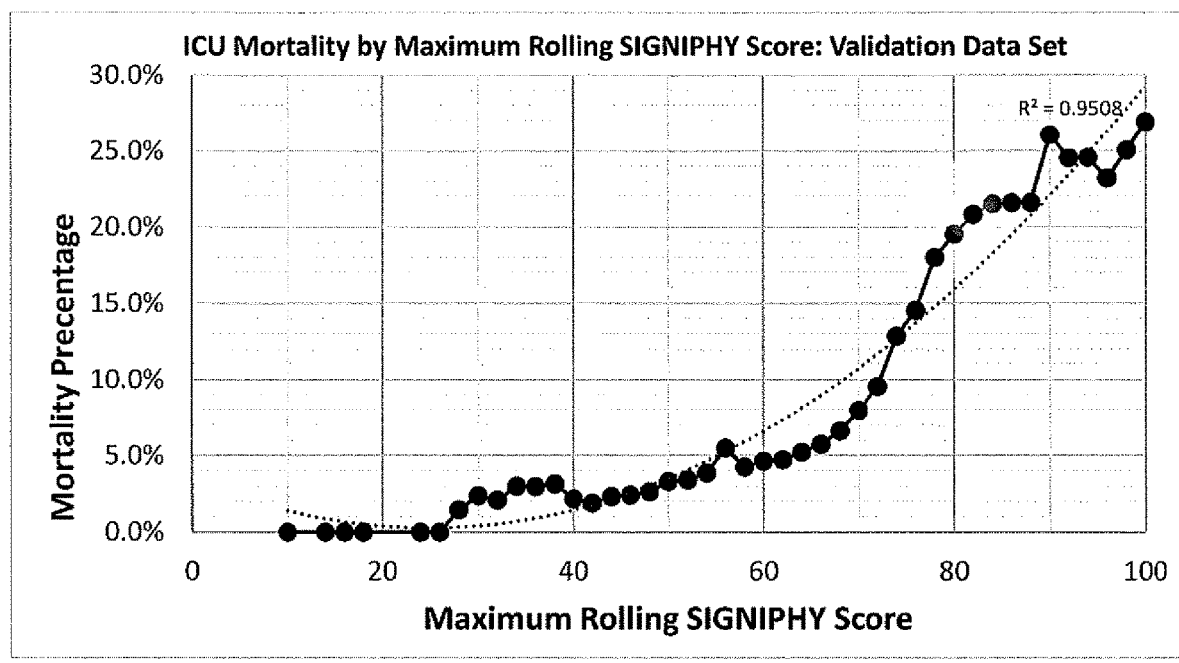

DYNAMIC ROLLING SEVENTY OF ILLNESS SCORE FOR A CRITICALLY ILL PATIENT

This application claims the benefit of U.S. Provisional Patent Application No. 62/779,694, filed Dec. 14, 2018, which is incorporated herein by reference in its entirety.

The present invention is a system and method primarily designed for use in an intensive care unit in a health care provider facility. The method and system, using patient physiological and clinical information, can monitor patients continually in near-real time and send an alert to a care-provider when a patient becomes at high risk for a deleterious outcome. A high-risk designation is based on the comparison of current and previous individual patient information to trends identified as deleterious in a database of historical patient information.

BACKGROUND

The intensive care unit (ICU) in an acute care hospital is a data rich environment. Almost all patients are hooked up to a bedside monitor, which yields high-frequency physiologic measurements. This lends itself to creating an ideal environment for collecting valuable physiologic and clinical information on patients over time. Further, outcomes such as mortality are much higher in the ICU than in other venues within an acute care hospital. While some at-risk patients are easily identified, others seem to be stabilized but then almost suddenly go into decline. It would be of considerable benefit to clinicians if these patients could be identified early enough in their clinical course to effect remedial treatment.

Numerous early warning scores (EWS) have been developed for the identification of patients with a high likelihood of admission to an intensive care unit or failing to survive. These include, among others, MEWS, NEWS, NEWS2, and SOFA. There have been varying levels of accuracy reported for these systems, but the consensus is that both sensitivity and specificity are less than desirable. In particular, the high number of false positives leads to "alarm fatigue", while many patients who deteriorate go undetected. Further, by themselves these systems are evaluated sporadically and don't incorporate previous time segments' values, i.e. they have no memory. Currently there is no scoring system with subsequent alerts for patients in an ICU.

Another prior system is described in a US patent application (Ser. No. 15/921,723, filed Mar. 15, 2018), incorporated by reference herein in its entirety, that describes a novel process for taking streaming physiologic data from an electronic medical record (EMR) system, assembling this data in a meaningful fashion, interpreting it in a way that permits alerts to be sent to clinicians caring for adult patients in an intensive care unit, and then generating such an alert. The alerts indicate that a patient is at a significantly higher risk of an adverse clinical outcome, e.g. mortality. This prior system is based on the first four hours of a patient's vital signs after admission to the ICU. However, this prior system does not have a memory. Only a single score over the first four hours post-admission is generated, therefore not taking into account changes in a patient's condition.

Hospitals have been increasingly calling for a continuous severity of illness score (SOIs) that generate alerts to notify clinicians of a significant change in their patient's condition. This is of utmost importance in the ICU, where patient frailty is high and can change rather quickly. There have been attempts to develop SOIs for the ICU, including Philips' Discharge Readiness Score and Emory University's modified APACHE score. Unfortunately, they suffer from some major drawbacks that preclude their implementation as an alert system:

1. Some of the information must be manually entered, which considerably delays SOI generation.
2. They are static in that they use scores at individual timepoints, rather than incorporate past scores in the calculation of the present score.
3. The scores are refreshed infrequently, instead of being updated relatively continuously or at least after short time intervals.
4. There is no translation of a score's value into an action taken by a clinician.

Prior attempts to generate continuous monitoring of patient acuity in the ICU have been of limited utility because of at least one or more of the following reasons: 1) a method included only one physiologic measure, e.g. heart rate; 2) traditional linear time series approaches were used to analyze data; 3) patterns of variability based on maximum entropy or fractal dimension were used (which have not proven to be highly predictive of patient deterioration); and 4) acuity scores were based on static measurements, rather than a dynamic use of current and prior physiologic values.

SUMMARY

The above deficiencies leave open the need for a continuous SOI that is based on high-frequency vital signs information, incorporating both current and past information. This invention describes a predictive analytics system that addresses the above deficiencies. It provides a novel multi-step system and process that inputs streaming vital signs data, identifies patterns in that data that are associated with a high risk of an adverse outcome, and then sends alerts to clinicians caring for those patients. Also included is whether a patient is currently receiving mechanical ventilation (or other clinical intervention) or has received it previously in his/her stay in the ICU. By utilizing the system and method, it is possible for clinicians to detect patients with a high risk of an adverse outcome in a timely fashion, enabling effective remedial treatment.

The method and system described herein present a novel way of incorporating vital signs information and whether a patient is on a mechanical ventilator or other clinical intervention into a process that creates a continuous, rolling severity of illness score. An alert is triggered whenever a patient's score crosses a threshold that indicates the patient is at medium and high risk, respectively, for an adverse outcome. When an alert is generated, it is sent to the mobile devices of clinicians caring for that patient.

This ability to detect physiologic indicators of decline before they become clinically manifested is of enormous benefit. By coupling an alert with a quick and appropriate response, it is hoped that further clinical deterioration is averted along with its associated morbidity, mortality and cost. This invention allows for the early detection of perilous physiologic patterns that result in an alert to clinical staff caring for that patient.

Another benefit of the method and system is that physicians would get a quick overview of each patient's fragility. This allows for stratifying patients by risk, which will facilitate a more orderly transition between intensivists when shifts change. Furthermore, in tele-ICU stations where anywhere from 30 to 150 patients' data are being displayed simultaneously, a color-coded addition to each patient's information allows intensivists to identify their most seriously ill patients in a timely manner.

The system and method are comprised of two phases. The first phase analyzes historical physiologic data from a hospital's EMR system and discovers data patterns that presage a deleterious outcome. These data patterns are stored in a first database. Once these patterns have been revealed, the second phase involves embedding these patterns into a hospital's EMR, collecting data on new patients in near-real time, matching up this data against the patterns uncovered in Phase One, and producing a score based on how many of these deleterious patterns a patient is exhibiting. This score is updated continuously, weighting the current value higher than previous scores. If this rolling score surpasses a specific value, an alert is generated. The alert, in one example a color-coded signal, is then sent to a mobile device or tablet of the clinicians caring for the patient.

The system and process described herein can identify patients at a high risk for deterioration long before the patient is clinically symptomatic. The ability to identify these patients early in their ICU stay may permit interventions that can reverse a patient's course. Further, this system and method stratify patients into risk categories, resulting in a color-coded alert sent to clinical staff caring for that patient. The color codes indicate the level of risk for that patient. The present methodology can be extended for use at other time points during a hospitalization for alerting other clinical outcomes: need for a specific clinical intervention (e.g. patient requires mechanical ventilation), readmission to the ICU, mortality in the hospital unit after a patient has been discharged from the ICU, etc.

The ability to detect physiologic indicators of decline before they become clinically manifested is of enormous benefit. By coupling an alert with a quick and appropriate response, it is hoped that that further clinical deterioration is averted along with its associated morbidity, mortality and cost. This invention allows for the early detection of perilous physiologic patterns that result in an alert to clinical staff caring for that patient. Therefore, the method and system described herein have the opportunity to provide valuable information to clinicians regarding their patient's condition throughout a patient's stay in the ICU. This process can be translated into computer code and embedded within a hospital's electronic medical record system.

This present system and method differ from earlier systems and methods of other EWS. First, it continually collects physiologic data in near-real time and uses that information throughout a patient's time in the ICU. Second, it includes information on whether a patient received mechanical ventilation or other clinical intervention and stores this information. Thus, even if a patient was previously on a ventilator and weaned off, he/she continues to accrue risk points. Current EWS simply record whether or not a patient is on a ventilator at that particular time point. That doesn't make sense clinically, because even if a patient was weaned off of a mechanical ventilator they are still at an increased risk; ventilator associated pneumonia and having to go back on a ventilator are distinct possibilities. Third, this invention is expandable, meaning it can have additional physiologic measurements and clinical interventions added to it as their importance becomes known. This is in contrast to all existing EWS, which are fixed in terms of the parameters in them and cannot be changed. Fourth, the score of the system and method herein is based on an exponential weighted moving average, so that previous scores are incorporated into the present score. Finally, when a patient's score crosses a pre-determined threshold value, a color-coded alert is sent to the clinician caring for that patient.

In one example, a method for identifying and managing high-risk patients comprises the steps of providing a clinical setting for a first patient wherein the setting includes a plurality of physiological monitors; providing an electronic device to a caregiver in the clinical setting; and providing a first database that stores historical measurements of a plurality of former patient physiological measurements and former patient outcomes of those former patients; defining trigger measurements based on the historical physiological measurements, wherein those trigger measurements represent a set of historical physiological measurements that have been identified as indicating a high risk for a negative clinical outcome. Next, the method includes providing a second database that receives and stores a plurality of measurements from the plurality of the first patient physiological monitors; and comparing the first patient physiological measurements to the first database of historical measurements to identify a high-risk patient based on whether the first patient set of physiological measurements correspond to the first database trigger measurements using an exponential moving average of the number of trigger measurements over time; to generate an acuity score that corresponds to the first patient's risk of an adverse event, wherein the exponential moving average is based on the first patient's current physiological measurements weighted more heavily than the first patient's previous physiological measurements. And finally, the method includes sending an alert to the caregiver via the electronic device if the first patient is at a high risk for a negative outcome based on the comparing step. The method may also include wherein the physiological measurements are selected from the group consisting of heart rate, respiratory rate, mean arterial pressure, saturated oxygen, temperature, glucose level, platelet count and white blood cell count, and whether or not the first patient has received or is receiving a clinical intervention; and also wherein the clinical intervention is selected from the group consisting of mechanical ventilation, receiving intravenous antibiotics, receiving vasopressors, receiving anti-hypertensive medications, and having a pacemaker inserted.

In another example, a system for identifying and managing high-risk patients comprises a clinical setting for a first patient wherein the setting includes a plurality of physiological monitors; an electronic device for a caregiver in the clinical setting; a first database that stores historical measurements in the clinical setting of a plurality of former patient physiological measurements and former patient outcomes of those former patients; and in the first database, a set of trigger measurements based on the historical physiological measurements, wherein those trigger measurements represent a set of historical physiological measurements that have been identified as indicating a high risk for a negative clinical outcome. The system also includes a second database that receives and stores a plurality of current measurements and previous measurements from the plurality of the first patient physiological monitors; a processor for comparing the first patient physiological measurements to the first database of historical measurements to identify a high-risk patient based on whether the first patient set of physiological measurements correspond to the first database trigger measurements using an exponential moving average of the number of trigger measurements over time to generate an acuity score that corresponds to the first patient's risk of an adverse event, wherein the exponential moving average is based on the first patient's current physiological measurements weighted more heavily than the first patient's previous physiological measurements; and an alert sent to the caregiver if the first patient is at a high risk for a negative outcome based on the comparing step.

In a still further example, a method for identifying and managing high-risk patients comprises the steps of providing a clinical setting for a first patient wherein the setting includes a plurality of physiological monitors; providing electronic devices to a caregiver in the clinical setting; providing a first database that stores historical measurements of a plurality of former patient physiological measurements, former patient clinical interventions, and former patient outcomes of those former patients; and defining trigger measurements based on the historical physiological measurements and historical clinical interventions, wherein those trigger measurements represent a set of historical physiological measurements and historical clinical interventions that have been identified as indicating a high risk for a negative clinical outcome. The method further includes providing a second database that receives and stores a plurality of measurements from the plurality of the first patient physiological monitors and also stores the occurrence of clinical interventions; comparing the first patient physiological measurements and clinical interventions to the first database of historical measurements to identify a high-risk patient based on whether the first patient set of physiological measurements and clinical interventions correspond to the first database trigger measurements; and sending an alert to the caregiver if the first patient is at a high risk for a negative outcome based on the comparing step.

BRIEF DESCRIPTION OF THE DRAWINGS

FIG. 1 is a schematic overview of the system and method described herein.

FIG. 2 is a graph demonstrating the association of an acuity score with mortality on a development set of ICU patients.

FIG. 3 is a graph demonstrating the validation of the relationship between acuity score and mortality on a set of ICU patients not included in the system's development.

DETAILED DESCRIPTION

The method and system described herein consist of two phases that result in the production of acuity scores, color-coded alerts within a hospital system's ICUs, and triggers for sending alerts to clinicians on their mobile devices. Each phase consists of specific steps: these are given below and illustrated in FIG. 1.

FIG. 1 is a schematic overview of the system and methods described herein. First Box 10 (Phase One) represents the historical physiological information collection and processing to identify high risk patterns and weights. This process begins with a hospital ICU 12 that includes multiple physiological monitors, and the historical patient information from those monitors is stored in the hospital EMR system 14. Using an analytical database 16, clinical endpoints are identified 18 and letters are assigned as described herein based on historical information. Patient vital sign data and whether or not they are or have been on a mechanical ventilator 20 are collected. High risk patterns and related acuity score 22 and weights assigned to vital signs 24 are then calculated, which information is then collected and saved. This historical patient information is then stored in the hospital EMR system 14. Second Box 25 (Phase Two) is the application of acuity score 22 and weights 24 to current ICU patients. Comparing with the historical database, a patient acuity score is calculated and continuously updated 27. If the patient's acuity score crosses a threshold value 29, then alerts 31 are sent to electronic devices to caregivers 32 as needed. The process is described in more detail in the following.

Phase One
1. Collect streaming physiologic data from an electronic medical record (EMR) system for patients admitted to an ICU, and segment them individually into bins that maximize the variation in mortality.
2. Create a mapping of patient data over consecutive time periods of the aforementioned bins into a symbolic representation ("letters").
3. Concatenate letters over consecutive time segments to form "words". Join these words with information on whether a patient is, or has been, in one example, on a mechanical ventilator or been subject to other clinical interventions.
4. Along with information on mechanical ventilation, ascertain which words are associated with increasing the risk of mortality.
5. Based on the number of words that increase risk, plus ventilator status, create a risk score that can be obtained for each patient. Find levels of scores that can be used as alerts.

Phase Two

6. Generate computer code for identifying the high-risk words. Embed this code into a hospital's EMR system for application to future patients.
7. As each patient enters an ICU, continually collect information on vital signs and mechanical ventilator status.
8. After four 30-minute segments, calculate an acuity score. Thereafter continually update this score with data from the current time period as well as data from previous periods.
9. Compare each score as it is generated with the threshold values obtained in Phase One. When an acuity score surpasses the first threshold, send a yellow-coded signal to the clinicians caring for that patient. If an acuity score surpasses the second threshold, send a red-coded signal to the clinicians caring for that patient. The alerts indicate that a patient is at a significantly higher risk of an adverse clinical outcome, e.g. mortality.

The following list of definitions are used throughout the description.

Physiologic measure: Any vital sign or lab measurement that gives information on a patient's medical condition. This may include, but is not limited to heart rate, respiratory rate, mean arterial pressure, $SaO_2$, and temperature. The analysis described herein includes both real-time or near real-time measurements referred to as "current" physiologic measurements and any similar previous measurements on the patient's medical condition.

Clinical intervention: Any therapeutic treatment applied to a patient by a medical caregiver. This includes, but is not limited to, mechanical ventilation (both current and previous), receiving intravenous antibiotics, receiving vasopressors, receiving anti-hypertensive medications, and having a pacemaker inserted.

Data point: A value for one physiologic measure at one point in time for a single patient. For example, a respiratory rate for John Doe taken on Mar. 3, 2017 at 1:00 am, a heart rate for Jim Smith taken on Mar. 3, 2017 at 6:35 am, a temperature for Sally Smith taken on Feb. 25, 2015 at 3:00 pm, etc . . . .

Outcome: A clinical endpoint such as mortality, length of stay, readmission, etc . . . .

Time Period: The duration of time over which physiologic measures are used to form a "Word" (see below). For example, if a patient is hospitalized for 3 days & four hours, and the time period is two hours, then that patient would have 38 words generated over the course of their hospitalization.

Time Segment: The duration of time over which physiologic measures are used to form a "Letter" (see below). For example, if a time period is two hours and four letters comprise a word, then the time segment is 30 minutes.

Personal Median: The median value of all data points for a physiologic measure for a single individual during a specific time segment. For example, John Doe's median heart rate over the first 30 minutes after admission, if a time segment is 30 minutes long.

Cut-points: Specific values within the overall range for a physiologic measurement that divide up the distribution into bins. For example, if heart rate ranges from 5 bpm to 140 bpm, and the cut-points are 30, 52, 75 and 100, then a heart rate value can be mapped to one of the following bins: minimum-30, 31-52, 53-75, 76-100 and 101-maximum. The bins are what define "Letters" (see below). Cut-points are derived by maximizing the mortality rates across bins ("Maximum Mortality Variability", see below).

Maximum Mortality Variability (MMV): For a physiologic measure, the distribution of bins that result in the maximum variability in mortality rate. This is derived from using a genetic algorithm or other optimization method to select the cut-points that maximize the pairwise difference in mortality rates between bins (differences expressed as absolute values).

Mathematically this is represented by optimizing the following function (Formula 1):

$$\Sigma_{i=1}^{n-1}\Sigma_{j=i+1}^{n}(\|m_i - m_j\|)/n \qquad \text{Formula 1.}$$

Where n=number of bins, $m_i$ is the mortality rate in bin "i", and $m_j$ is the mortality rate in bin j. For example, suppose respiratory rates ranged from 8-60, and two sets of cut-points yielded the following bins as shown in Table 1:

TABLE 1

Mortality rates for two hypothetical set of bins: respiratory rate values. The mortality variability for Bins #1 is 0.132 while the mortality variability for Bins #2 is 0.147.

| Bins #1 | Mortality rate | Bins #2 | Mortality Rate |
|---|---|---|---|
| 2-8 | 0.20 | 2-19 | 0.05 |
| 9-16 | 0.07 | 20-24 | 0.03 |
| 17-22 | 0.02 | 25-60 | 0.25 |
| 23-45 | 0.24 | | |
| Mortality Variability | (.13 + .18 + .04 + .05 + .17 + .22)/6 = .132 | | (.02 + .20 + .22)/3 = 0.147 |

Since Bins #2 have a higher mortality variability than Bins #1, it is the MMV. In practice the number of possible bins will be large, and thus a genetic algorithm is used to find the bins with the MMV. Note that the number of cut-points is not fixed at a specific number.

Letter: A letter is assigned based on the personal median of a physiologic measure for a predetermined time segment. For example, if a time segment is 30 minutes, there would be a letter assigned every 30 minutes. The assignment of letters is based on which bin a patient's personal median falls within for a specific physiologic measure. Consequently, the number of letters is determined by the number of cut-points: the former is always one greater than the latter. An example is shown in Table 2. Suppose heart rate had the following cut-points: 32, 50, 76 and 105. This would yield bins of minimum-32, 33-50, 51-76, 77-105, and 106-maximum. A personal median heart rate of 28 would get assigned a letter of "A", a personal median heart rate of 49 would get assigned a letter of "B", etc. The assigned order of letters is not important and does not convey any information. In fact, letters could be any symbol, e.g. "%", "#", etc. The key point is that a letter/symbol denotes a specific range of physiologic values.

TABLE 2

Hypothetical assignment of letters to bins of median heart rates

| Cut-Point | Resulting Bin | Letter |
|---|---|---|
| 32 | Minimum-32 | A |
| 50 | 33-50 | B |
| 76 | 51-76 | C |
| 105 | 77-105 | D |
| | 196-Maximum | E |

Word: A combination of letters formed over a specified time period. If the time period includes all data points collected over the course of two hours, and letters are formed every 30 minutes, then a word would consist of four letters. The next two hours would generate another word.

Smoothing factor: The amount of weight placed on a current time period's score versus the previous time period's score. Formula 2 shows how a final score at time t is derived from the exponential weighted average of the current time period's score and the previous time period score(s):

$$\text{Final Score}_t = \omega * (\text{Score}_t) + (1-\omega) * (\text{Final Score}_{t-1}), \qquad \text{Formula 2.}$$

where $0.1 \leq \omega \leq 0.9$. A value of $\omega=0.5$ means that equal weight is placed on the score at this time period and the final score from the previous time periods. $\omega$ is not pre-determined, but obtained as a result of the optimization process that determines influential words. For the purposes of calculation of an acuity score as described herein, a patient's current physiologic measurements and the existence or not of a clinical intervention is weighted more heavily than the patient's previous physiologic measurements and clinical interventions.

Trigger: A word that significantly increases the chance of an outcome, e.g. mortality.

Alert: Signal sent to clinicians' mobile phones or tablets when one of their patients has at least one trigger. In one example, the graphic for an alert is color coded based on the number of triggers.

Example

The following research study will be used to illustrate how the present system and method are generated, and is referred to as the "STUDY". Of course, other databases and information could alternatively be used and are expected to be used in a similar manner as described here.

Fourteen hospitals submitted data to a commercial centralized database ("Phoenix", Medical Decision Network, Charlottesville, Va.) for admissions to 32 ICUs during the timeframe of January 2012 through October 2017. This comprised 59,399 admissions. Data were continuously obtained on each patient for heart rate, respiratory rate, mean arterial pressure, start/stop times for mechanical ventilation, and mortality before discharge from the ICU. The 40,046 admissions from 2012 through 2015 were used to identify significant word patterns (i.e., the development data set), while the 19,353 admissions from the rest of the years were used to validate those results.

It was decided a priori that the time segment for a letter would be 30 minutes, and the time period for a word would be two hours: four letters. The reason for selecting two hours is that it is likely the longest amount of time a clinician would want to wait for a potential alert to be generated. (In the situation where bedside monitors are consistently yielding data points, then alternatively a much smaller time segment is possible and indeed desirable.) The objective was to identify influential words that significantly increased the probability of a patient dying in the ICU at any time from two hours post-admission to the unit, and to create an acuity score based on these results.

PHASE 1

Step One: Determination of the Cut-Points and Optimal Bins

The initial step involved calculating the median values for heart rate, respiratory rate, and mean arterial pressure, respectively every 30 minutes for each patient. Once the median values were obtained, data from the first four medians (i.e. first four time segments=two hours) were selected. Optimal bins were created for each vital sign by finding ranges that according to Formula 1 above resulted in the maximum mortality variability. The resulting cut-points and optimal bins are given below:

Heart rate had three cut-points that defined optimal bins: 85, 122, & 140. The four bins had mortality rates of 4.3%, 7.4%, 13.3%, and 18.8%.

Respiratory rate had three cut-points that defined optimal bins: 18, 32, & 37. The four bins had mortality rates of 3.9%, 7.9%, 16.3%, and 15.0%.

Mean arterial pressure had four cut-points that defined optimal bins: 53.8, 61.9, 73.6, and 81.5. The five bins had mortality rates of 32.2%, 15.9%, 8.8%%, 5.6%, and 4.1%.

Step 2: Assigning Letters to the Optimal Bins

Table 3 shows the letters assigned to the optimal bins for each vital sign. It is important to note that the letters simply identify an optimal bin; they have no other intrinsic value of their own. For example, "A" for heart rate indicates the median value is in the fourth optimal bin, while for respiratory rate a value of "A" is for the third optimal bin. Letters need not be used; any alphanumeric symbol would suffice.

TABLE 3

Assignment of letters to optimal bins for each vital sign

| Heart Rate Optimal Bins | Letters | Respiratory Rates Optimal Bins | Letters | Mean Arterial Pressure Optimal Bins | Letters |
|---|---|---|---|---|---|
| 5-85 | Z | 3-18 | X | 30.0-53.8 | W |
| 86-122 | Y | 19-31 | N | 53.9-61.8 | V |
| 123-139 | B | 32-36 | A | 61.9-73.5 | P |
| 140-210 | A | 37-90 | Q | 73.6-81.4 | D |
| N/A | N/A | N/A | N/A | 81.5-200 | B |

Here are some examples for a patient with the median values given below:

A median heart rate of 90 would get a letter Y assigned to it (second optimal bin).

A median respiratory rate of 15 would get a letter X assigned to it (first optimal bin).

A median mean arterial pressure of 83 would get a letter B assigned to it (fifth optimal bin).

The above process is carried out for every time segment for each patient.

Step 3: Forming Words from Letters

After assignment of letters, words are formed by concatenating the letters from four consecutive time segments The first four letters were used to assign a word to a patient. After that time period the next four letters are used to form another word, and so on. This would continue until the patient died, was discharged from the ICU, or stayed seven days in the ICU: whichever came first. The number of words for a patient was equal to the patient's length of stay in the ICU*48. For example, if a patient stayed in the ICU for 4.2 days and then expired, that patient would receive 4.2*12=50.4, i.e. 50 words. If a patient stayed longer than seven days in the ICU his/her number of words would max out at 84, then remain at the 84th word throughout the remainder of the ICU stay.

Example: A patient had 30-minute median heart rates for the first four hours of 80, 122, 120, 120, 126, 110, 95, and 84. Using Table 3 above, that patient would have the four-hour time span's two words=ZYYY and BYYA.

Step 4: Ascertain which Words are Associated with Mortality and Assign Weights.

Words are generated for every patient for each vital sign across their time in the ICU (up to seven days). Each specific word (e.g. ZYYA, AYZZ, BAZB, etc. . . . ) is randomly assigned a weight of 0, 1, or 2. So for a specific time period a patient will have three weights: one for heart rate, one for respiratory rate, and another for mean arterial pressure. In addition, patients are also given a weight=2 if they are currently on a mechanical ventilator or a weight=1 if they were previously on a mechanical ventilator. As long as a patient has not been placed on a mechanical ventilator then he/she gets a mechanical ventilation weight=0. Additional clinical interventions may additionally or alternatively be given weight and incorporated in the calculation. Therefore, in this example, a patient can have a sum of weights ranging from 0 to 8 for the first time period.

Starting with time period #2, the assignment of weights is slightly modified to take account of the previous time period. For each vital sign, the weight assigned to a patient is the maximum of the weight from the current time period and the previous time period. These weights are summed as was done in the first time period. To further accentuate the importance of previous time periods, a smoothing factor is added as was shown in Formula 2. The Starting with time period #2, a patient's Final Score is given in Formula 3.

$$\text{Final Score}_t = \omega*(\Sigma \max(w_t, w_{t-1})) + (1-\omega)*(\text{Final Score}_{t-1}), \quad \text{Formula 3.}$$

Where $w_t$ is the weight at time t for heart rate, respiratory rate, mean arterial pressure, and ventilation status, and $w_{t-1}$ is the weight for the preceding time period; $\omega$ is the smoothing factor as described in Formula 2 above.

Thus, Final Scorer is still within the range 0-8, but it is now a continuously distributed parameter. As mentioned above, each heart rate word, respiratory rate word, and mean arterial pressure word randomly assigned a value of 0, 1, or 2; $\omega$ is initially a randomly assigned number between 0.1 and 0.9.

The maximum score over all time periods for a patient is obtained; Final Score(max). Then a genetic algorithm is used to find the set of weights that optimize a patient's Final Score (max) with mortality. (Previously the weights were randomly assigned.) That is, the weights are adjusted so that increasing maximum scores correlate with increasing mortality. This entails optimizing hundreds of weights simultaneously. The genetic algorithm has a further component in that patients with a low score who died (false negative) were penalized more than patients with a high score who survived (false positive). The end result of the genetic algorithm optimization is that every heart rate word, respiratory rate word, and mean arterial pressure word has a final value of 0, 1, or 2. ω is also stabilized at a value between 0.1-0.9. These values can be used to calculate future patients' scores continuously every 30 minutes.

Step 5. Resealing the Final Scores to a 0-100 Range, and Determining Risk Levels In order to make the score intuitive for clinicians, it is resealed to lie between 0 and 100. In the present example, the raw score went from 0.00-8.00, so the resealed score is simply 12.5 times the raw score. From the resealed scores, finding levels that demarcate medium risk, high risk, and urgent risk is straightforward. The maximum score for each patient is obtained, and then are rank-ordered from lowest to highest across the 40,046 patients in the development data set. The mortality rate is calculated for every 5% quantity of patients. Then a plot is created that has the mean score for each 5% quantity of patients on the x-axis and the corresponding mortality rate on the y-axis. The plot from our example is shown in FIG. 2.

There is a strong second-order polynomial relationship between patients' maximum score and mortality rate ($r^2$=0.961). It is clear that the mortality rate starts to increase rapidly when scores rise above 64, then increase further at scores above 84. These inflections in the mortality curve are assigned the following alerts:

If at any time a patient's score reaches 65, send out a "moderate risk" alert.

If the score reaches 85 send out a "high risk" alert.

These alerts can be color-coded symbols in yellow and red, respectively. The purpose of the alerts is to notify the clinician that their patient is at an elevated risk of mortality and that compensatory treatment should be highly considered. A patient might receive a yellow moderate risk alert at one time period, then have a red high-risk alert sent at a succeeding time point. Alternative and additional visual indicia may be used to send and highlight alerts that are sent. These additional indicia include blinking lights, variable intensity in the color, different colors, and other visual indicia appearing on a screen. Still further additionally or alternatively, audible signals may be sent as warning to the electronic devices in the ICU and the mobile devices of caregivers.

The results from using the development data set to set the weights and score the patients are impressive. However, the true test of a predictive process is to validate the weights against a new set of data. Thus, data from the 19,353 patients in the validation data set were scored using the set of weights determined for the development data set. FIG. 3 shows the same type of graph as FIG. 2, but using patients from the validation data set. The results are almost identical to those seen in the development data set. Step 5 was the final part of Phase 1. The next steps are included in Phase 2, where the results from Phase 1 are applied to new patients in simultaneous or near-real time.

PHASE 2

Step 6. Generate Computer Code for Identifying the High-Risk Words. Embed this Code into a Hospital's EMR System for Application to Future Patients.

In this step, the sixth overall but the first in Phase 2, the words and their respective weights are encoded within a hospital's electronic medical record (EMR) system. This might be within an ICU database, bedside monitor that collects clinical information, or the actual underlying EMR system.

Step 7. As Each Patient Enters an ICU, Continually Collect Information on Vital Signs and Mechanical Ventilator Status.

As each patient enters an ICU, values for all vital signs as well as mechanical ventilation status are sent via HL-7 feeds to the present system. This is a continuous stream of data that is sampled frequently. At 30 minutes after admission to the ICU, the median value for each vital sign is internally calculated for each patient to form letters corresponding to those median values. This process continues for each 30 minutes thereafter. An HL-7 feed is also set up with the EMR to gather the start and stop times of a patient receiving mechanical ventilation.

Step 8. After Four Complete Time Segments, Start Constructing Words. Calculate an Acuity Score and Continually Update.

After four 30-minute segments post-admission have transpired for a patient, form words based on the letters from each time segment. From the words' weights as well as mechanical ventilation status, an acuity score is calculated. Thereafter continually update this score with data from the preceding time period as well as data from previous periods (weighted less than the preceding period).

Step 9. Compare Each Score as it is Generated with the Threshold Values Obtained in Phase 1, and Generate Alerts if Appropriate.

After each score is generated, it is compared with the threshold values obtained in Phase 1. If an acuity score surpasses the first threshold, a yellow-coded signal is sent to the clinicians caring for that patient. When an acuity score surpasses the second threshold, a red-coded signal is sent to the clinicians caring for that patient. The alerts indicate that a patient is at a significantly higher risk of an adverse clinical outcome, e.g. mortality. Starting with the end of the first time period a score is generated, and a new score is generated every time period up to seven days (84 time periods). After seven days the last score carries over throughout the remainder of the patient's ICU stay.

Other embodiments of the present invention will be apparent to those skilled in the art from consideration of the specification. It is intended that the specification and figures be considered as exemplary only, with a true scope and spirit of the invention being indicated by the claims.

That which is claimed is:

1. A method for identifying and managing high-risk patients comprising the steps of:
   providing a clinical setting for a first patient wherein the setting includes a plurality of physiological monitors;
   providing an electronic device to a caregiver in the clinical setting;
   providing a first database that stores historical measurements of a plurality of former patient physiological measurements and former patient outcomes of those former patients wherein for each historical physiological measurement, dividing up the physiological measurements into ranges to form bins, wherein a distribution of bins results in the maximum variability in the historical mortality outcome rate;
   wherein each bin is assigned a different letter;
   defining trigger measurements based on the historical physiological measurements, wherein those trigger measurements represent early detection of perilous physiologic patterns in a set of historical physiological measurements that have been identified as indicating a high risk for a future negative clinical patient outcome;

providing a second database that receives and stores a plurality of first patient physiological measurements from the plurality of the first patient physiological monitors;

wherein the first patient physiological measurements occur at regular time segments; and wherein the letter is assigned for each time segment for each physiological measurement depending on which bin the physiological measurement is in;

wherein the letters assigned for each first patient current time period and previous time period physiological measurement are saved, and the letters are collected for a predetermined time period which is comprised of a plurality of time segments;

wherein the plurality of letters associated with each time period form a word, and further wherein the trigger is the word that indicates an increase in a chance of a negative patient outcome;

wherein the word from the current time period and the word from the previous time period are used to detect if any words result in a trigger; and comparing the first patient physiological measurements to the first database of historical measurements to identify a high-risk patient based on whether the first patient set of physiological measurements correspond to the first database trigger measurements using an exponential moving average of the number of trigger measurements over time to generate an acuity score that corresponds to the first patient's risk of an adverse event, wherein the exponential moving average is based on the first patient's current physiological measurements weighted more heavily than the first patient's previous physiological measurements; and sending an alert to the caregiver via the electronic device if the first patient is at a moderate or high risk for a negative outcome based on the comparing step.

2. The method for identifying and managing high-risk patients as described in claim 1,
wherein the physiological measurements are selected from the group consisting of heart rate, respiratory rate, mean arterial pressure, saturated oxygen, temperature, glucose level, platelet count and white blood cell count, and whether or not the first patient has received or is receiving a clinical intervention.

3. The method for identifying and managing high-risk patients as described in claim 2,
wherein the clinical intervention is selected from the group consisting of mechanical ventilation, receiving intravenous antibiotics, receiving vasopressors, receiving anti-hypertensive medications, and having a pacemaker inserted.

4. The method for identifying and managing high-risk patients as described in claim 1,
wherein the physiological measurements are recorded and saved for each of a predetermined time segment.

5. The method for identifying and managing high-risk patients as described in claim 1,
wherein the first patient physiological measurements occur at regular time segments.

6. The method for identifying and managing high-risk patients as described in claim 5,
wherein each time segment is from about 1 to 30 minutes.

7. The method for identifying and managing high-risk patients as described in claim 1,
further wherein the first patient is receiving clinical intervention during a specific time period the trigger is generated; and wherein if the first patient is not receiving clinical intervention during a specific time period but previously did then the trigger is generated.

8. The method for identifying and managing high-risk patients as described in claim 1,
wherein the alert sent to the caregiver comprises visual indicia sent to a user interface on the caregiver electronic device with respect to the specific patient.

9. The method for identifying and managing high-risk patients as described in claim 1,
wherein the alert sent to the caregiver comprises a visual and audible sound sent to the caregiver electronic device with respect to the specific patient.

10. The method for identifying and managing high-risk patients as described in claim 1,
wherein the word has four letters.

11. A system for identifying and managing high-risk patients comprising:
a clinical setting for a first patient wherein the clinical setting includes a plurality of physiological monitors;
an electronic device for a caregiver in the clinical setting;
a first database that stores historical measurements in the clinical setting of a plurality of former patient physiological measurements and former patient outcomes of those former patients;
wherein for each historical physiological measurement, dividing up the physiological measurements into ranges to form bins, wherein the distribution of bins results in the maximum variability in the historical mortality outcome rate;
wherein each bin is assigned a different letter;
in the first database, a set of trigger measurements based on early detection of perilous physiologic patterns in the historical physiological measurements, wherein those trigger measurements represent a set of historical physiological measurements that have been identified as indicating a high risk for a future negative patient outcome;
a second database that receives and stores a plurality of current first patient physiological measurements and previous first patient physiological measurements from the plurality of the first patient physiological monitors;
wherein the first patient physiological measurements occur at regular time segments; and
wherein a letter is assigned for each time segment for each physiological measurement depending on which bin the physiological measurement is in;
wherein the letters assigned for each first patient current time period and previous time period physiological measurement are saved, and the letters are collected for a predetermined time period which is comprised of a plurality of time segments;
wherein the plurality of letters associated with each time period form a word, and further wherein the trigger is the word that indicates an increase in a chance of a negative patient outcome;
wherein the word from the current time period and the word from the previous time period are used to detect if any words result in a trigger;
a processor for comparing the first patient physiological measurements to the first database of historical measurements to identify a high-risk patient based on whether the first patient set of physiological measurements correspond to the first database trigger measurements using an exponential moving average of the number of trigger measurements over time to generate an acuity score that corresponds to the first patient's risk of an adverse event, wherein the exponential moving average is based on the first patient's current physiological measurements weighted more heavily than the first patient's previous physiological measurements; and an alert sent to the caregiver if the first patient is at a high risk for a negative outcome based on the comparing step.

12. The system for identifying and managing high-risk patients as set forth in claim 11, wherein the alert sent to the caregiver comprises visual indicia sent to a user interface on the caregiver electronic device with respect to the specific patient.

13. The system for identifying and managing high-risk patients as set forth in claim 11, wherein the processor derives the acuity score by exponentially smoothing the value from the current time period with a smoothed value from previous time periods;

wherein a score is generated and resealed to fall between 0 and 100;

wherein the maximum score for all patients in the first database is plotted as deciles of risk for mortality;

wherein the graph of plotted deciles is examined for inflection points that indicate a significant increase in risk; and wherein those inflection points are used to generate color-coded icons for each patient that are displayed on a clinical setting board of all patients.

14. A method for identifying and managing high-risk patients comprising the steps of:

providing a clinical setting for a first patient wherein the setting includes a plurality of physiological monitors;

providing electronic devices to a caregiver in the clinical setting;

providing a first database that stores historical measurements of a plurality of former patient physiological measurements, former patient clinical interventions, and former patient outcomes of those former patients;

wherein for each historical physiological measurement, dividing up the physiological measurements into ranges to form bins, wherein the distribution of bins results in the maximum variability in the historical mortality outcome rate;

wherein each bin is assigned a different letter;

defining trigger measurements based on the historical physiological measurements and historical clinical interventions, wherein those trigger measurements represent early detection of perilous physiologic patterns in a set of historical physiological measurements and historical clinical interventions that have been identified as indicating a high risk for a future negative patient clinical outcome;

providing a second database that receives and stores a plurality of first patient physiological measurements from the plurality of the first patient physiological monitors and also stores the occurrence of clinical interventions;

wherein the first patient physiological measurements occur at regular time segments; and wherein the letter is assigned for each time segment for each physiological measurement depending on which bin the physiological measurement is in wherein the letters assigned for each first patient current time period and previous time period physiological measurement are saved, and the letters are collected for a predetermined time period which is comprised of a plurality of time segments;

wherein the plurality of letters associated with each time period form a word, and further wherein the trigger is the word that indicates an increase in a chance of a negative patient outcome;

wherein the word from the current time period and the word from the previous time period are used to detect if any words result in a trigger; and comparing the first patient physiological measurements and clinical interventions to the first database of historical measurements to identify a high-risk patient based on whether the first patient set of physiological measurements and clinical interventions correspond to the first database trigger measurements; and sending an alert to the caregiver if the first patient is at a high risk for a negative outcome based on the comparing step.

\* \* \* \* \*

UNITED STATES PATENT AND TRADEMARK OFFICE
CERTIFICATE OF CORRECTION

| | |
|---|---|
| PATENT NO. | : 11,443,853 B2 |
| APPLICATION NO. | : 16/595540 |
| DATED | : September 13, 2022 |
| INVENTOR(S) | : Andrew Alan Kramer |

It is certified that error appears in the above-identified patent and that said Letters Patent is hereby corrected as shown below:

On the Title Page

Item (54), Title, please delete "Seventy" and insert -- Severity --.

In the Specification

Column 1, Line 1, in the Title, please delete "Seventy" and insert -- Severity --.

Signed and Sealed this
Twentieth Day of December, 2022

*Katherine Kelly Vidal*

Katherine Kelly Vidal
*Director of the United States Patent and Trademark Office*